United States Patent
Ibrahim et al.

(10) Patent No.: US 10,136,909 B2
(45) Date of Patent: Nov. 27, 2018

(54) MAGNETIC INTRODUCER SYSTEMS AND METHODS

(75) Inventors: Tamer Ibrahim, Danville, CA (US); Michael J. Banchieri, Discovery Bay, CA (US); Dwight P. Morejohn, Davis, CA (US)

(73) Assignee: AtriCure, Inc., Mason, OH (US)

( * ) Notice: Subject to any disclaimer, the term of this patent is extended or adjusted under 35 U.S.C. 154(b) by 1091 days.

(21) Appl. No.: 12/339,331

(22) Filed: Dec. 19, 2008

(65) Prior Publication Data

US 2009/0163768 A1 Jun. 25, 2009

Related U.S. Application Data

(60) Provisional application No. 61/015,472, filed on Dec. 20, 2007.

(51) Int. Cl.
| | |
|---|---|
| *A61B 1/00* | (2006.01) |
| *A61B 17/29* | (2006.01) |
| *A61B 17/34* | (2006.01) |
| *A61B 5/06* | (2006.01) |
| *A61B 18/14* | (2006.01) |
| *A61B 17/00* | (2006.01) |

(Continued)

(52) U.S. Cl.
CPC .............. *A61B 17/29* (2013.01); *A61B 5/062* (2013.01); *A61B 17/3421* (2013.01); *A61B 5/06* (2013.01); *A61B 18/1492* (2013.01); *A61B 90/361* (2016.02); *A61B 2017/00247* (2013.01); *A61B 2017/00296* (2013.01); *A61B 2017/00331* (2013.01); *A61B 2017/00477* (2013.01); *A61B 2017/00876* (2013.01); *A61B 2017/2933* (2013.01); *A61B 2017/2944* (2013.01); *A61B 2018/00392* (2013.01); *A61B 2018/1495* (2013.01); *A61B 2090/3614* (2016.02)

(58) Field of Classification Search
CPC ............ A61B 1/00087; A61B 1/00101; A61B 1/00112; A61B 1/00158; A61B 1/00098
USPC ........ 600/104, 153, 125, 127, 129; 604/114; 606/32, 46, 47
See application file for complete search history.

(56) References Cited

U.S. PATENT DOCUMENTS

| | | | | |
|---|---|---|---|---|
| 2,623,256 A | * | 12/1952 | Feibelman ........... | A44C 5/2076 24/303 |
| 3,111,736 A | * | 11/1963 | Budreck .............. | A44B 15/002 24/303 |

(Continued)

OTHER PUBLICATIONS

Borst, Cornelius, et al., "Coronary artery bypass grafting without cardiopulmonary bypass and without interruption of native coronary flow using a novel anastomosis site restraining device ("Octopus")," JACC vol. 27, No. 6, May 1996, pp. 1356-1364.

(Continued)

*Primary Examiner* — Timothy J Neal
(74) *Attorney, Agent, or Firm* — Levine Bagade Han LLP

(57) ABSTRACT

Systems and methods for placing a treatment device within a patient involve advancing a magnetic first introducer into the patient, advancing a magnetic second introducer into the patient, coupling the first introducer with the second introducer via magnetic force, and using the introducer devices to place a treatment device at a desired location within the patient. Optionally, such techniques involve visualization of the introducers or treatment devices during the procedure.

14 Claims, 17 Drawing Sheets

(51) Int. Cl.
*A61B 18/00* (2006.01)
*A61B 90/00* (2016.01)

(56) References Cited

U.S. PATENT DOCUMENTS

| | | | |
|---|---|---|---|
| 3,129,477 A * | 4/1964 | Mizuno | A44C 5/2076 24/303 |
| 3,745,998 A | 7/1973 | Rose | |
| 3,986,493 A * | 10/1976 | Hendren, III | 600/12 |
| 4,190,041 A * | 2/1980 | Chikama | A61B 1/00098 600/104 |
| 4,224,929 A | 9/1980 | Furihata | |
| 4,445,892 A | 5/1984 | Hussein et al. | |
| 4,961,738 A | 10/1990 | Mackin | |
| 4,991,578 A | 2/1991 | Cohen | |
| 5,025,778 A * | 6/1991 | Silverstein et al. | 600/104 |
| 5,122,137 A * | 6/1992 | Lennox | 606/40 |
| 5,336,252 A | 8/1994 | Cohen | |
| 5,409,483 A | 4/1995 | Campbell et al. | |
| 5,423,805 A | 6/1995 | Brucker et al. | |
| 5,503,617 A | 4/1996 | Jako | |
| 5,593,405 A | 1/1997 | Osypka | |
| 5,672,153 A | 9/1997 | Lax et al. | |
| 5,681,260 A * | 10/1997 | Ueda et al. | 600/114 |
| 5,727,569 A | 3/1998 | Benetti et al. | |
| 5,782,746 A | 7/1998 | Wright | |
| 5,807,243 A | 9/1998 | Vierra et al. | |
| 5,836,311 A | 11/1998 | Borst et al. | |
| 5,865,730 A | 2/1999 | Fox et al. | |
| 5,927,284 A | 7/1999 | Borst et al. | |
| 5,976,132 A | 11/1999 | Morris | |
| 6,013,027 A | 1/2000 | Khan et al. | |
| 6,015,378 A | 1/2000 | Borst et al. | |
| 6,036,641 A | 3/2000 | Taylor et al. | |
| 6,036,685 A | 3/2000 | Mueller | |
| 6,039,733 A | 3/2000 | Buysse et al. | |
| 6,071,233 A * | 6/2000 | Ishikawa et al. | 600/104 |
| 6,086,586 A | 7/2000 | Hooven | |
| 6,110,106 A | 8/2000 | MacKinnon et al. | |
| 6,161,543 A | 12/2000 | Cox et al. | |
| 6,237,605 B1 * | 5/2001 | Vaska et al. | 128/898 |
| 6,251,065 B1 | 6/2001 | Kochamba et al. | |
| 6,277,065 B1 | 8/2001 | Donofrio | |
| 6,309,349 B1 | 10/2001 | Bertolero et al. | |
| 6,328,688 B1 | 12/2001 | Borst et al. | |
| 6,334,843 B1 | 1/2002 | Borst et al. | |
| 6,336,898 B1 | 1/2002 | Borst et al. | |
| 6,338,712 B2 | 1/2002 | Spence et al. | |
| 6,338,738 B1 | 1/2002 | Bellotti et al. | |
| 6,346,077 B1 | 2/2002 | Taylor et al. | |
| 6,350,229 B1 | 2/2002 | Borst et al. | |
| 6,352,534 B1 | 3/2002 | Paddock et al. | |
| 6,364,826 B1 | 4/2002 | Borst et al. | |
| 6,371,906 B1 | 4/2002 | Borst et al. | |
| 6,390,976 B1 | 5/2002 | Spence et al. | |
| 6,394,948 B1 | 5/2002 | Borst et al. | |
| 6,463,332 B1 | 10/2002 | Aldrich | |
| 6,464,630 B1 | 10/2002 | Borst et al. | |
| 6,482,151 B1 | 11/2002 | Vierra et al. | |
| 6,484,727 B1 | 11/2002 | Vaska et al. | |
| 6,511,416 B1 | 1/2003 | Green, II et al. | |
| 6,514,250 B1 | 2/2003 | Jahns et al. | |
| 6,522,905 B2 | 2/2003 | Desai | |
| 6,524,338 B1 | 2/2003 | Gundry | |
| 6,527,767 B2 | 3/2003 | Wang et al. | |
| 6,544,263 B2 | 4/2003 | Morgan et al. | |
| 6,595,989 B1 | 7/2003 | Schaer | |
| 6,599,237 B1 | 7/2003 | Singh | |
| 6,645,202 B1 | 11/2003 | Pless et al. | |
| 6,652,518 B2 | 11/2003 | Wellman et al. | |
| 6,758,809 B2 | 7/2004 | Briscoe et al. | |
| 6,778,846 B1 * | 8/2004 | Martinez | A61B 19/52 600/407 |
| 6,849,075 B2 | 2/2005 | Bertolero et al. | |
| 6,878,106 B1 * | 4/2005 | Herrmann | 600/104 |
| 6,890,295 B2 | 5/2005 | Michels et al. | |
| 7,018,328 B2 | 3/2006 | Mager et al. | |
| 7,204,207 B2 * | 4/2007 | Hurwitz | A01K 27/006 119/795 |
| 7,226,448 B2 | 6/2007 | Bertolero et al. | |
| 7,237,555 B2 | 7/2007 | Kochamba et al. | |
| 7,282,057 B2 * | 10/2007 | Surti et al. | 606/153 |
| 7,338,434 B1 | 3/2008 | Haarstad et al. | |
| 7,431,694 B2 * | 10/2008 | Stefanchik et al. | 600/104 |
| 7,441,917 B1 * | 10/2008 | Underdown | A44C 15/0015 362/103 |
| 7,542,807 B2 | 6/2009 | Bertolero et al. | |
| 7,566,300 B2 * | 7/2009 | Devierre et al. | 600/104 |
| 7,575,548 B2 * | 8/2009 | Takemoto et al. | 600/104 |
| 7,594,915 B2 | 9/2009 | Kochamba et al. | |
| 7,608,038 B2 * | 10/2009 | Ginsberg | 600/104 |
| 7,976,458 B2 * | 7/2011 | Stefanchik et al. | 600/104 |
| 2002/0026094 A1 | 2/2002 | Roth | |
| 2002/0056460 A1 | 5/2002 | Boyd | |
| 2002/0068855 A1 | 6/2002 | Daniel et al. | |
| 2002/0099270 A1 | 7/2002 | Taylor et al. | |
| 2002/0099390 A1 | 7/2002 | Kaplan | |
| 2002/0177846 A1 | 11/2002 | Mulier et al. | |
| 2003/0009080 A1 | 1/2003 | Peng et al. | |
| 2003/0010346 A1 | 1/2003 | Paolitto et al. | |
| 2003/0060685 A1 | 3/2003 | Houser et al. | |
| 2003/0158463 A1 | 8/2003 | Julian et al. | |
| 2003/0158464 A1 | 8/2003 | Bertolero | |
| 2003/0229974 A1 * | 12/2003 | Zemer | A44C 5/2076 24/303 |
| 2004/0154143 A1 * | 8/2004 | Harrell | A44C 5/2076 24/303 |
| 2004/0186350 A1 * | 9/2004 | Brenneman et al. | 600/146 |
| 2005/0010179 A1 | 1/2005 | Bertolero et al. | |
| 2005/0119653 A1 | 6/2005 | Swanson | |
| 2005/0119654 A1 | 6/2005 | Swanson et al. | |
| 2005/0240175 A1 | 10/2005 | Bertolero et al. | |
| 2006/0015165 A1 | 1/2006 | Bertolero et al. | |
| 2006/0063973 A1 * | 3/2006 | Makower et al. | 600/114 |
| 2006/0123845 A1 * | 6/2006 | Beard | A44C 5/2076 63/3.1 |
| 2006/0155272 A1 | 7/2006 | Swanson | |
| 2006/0235372 A1 * | 10/2006 | Ward | A61B 18/1492 606/13 |
| 2007/0233226 A1 | 10/2007 | Kochamba et al. | |
| 2008/0294154 A1 | 11/2008 | Ibrahim et al. | |
| 2009/0048591 A1 | 2/2009 | Ibrahim et al. | |
| 2009/0076501 A1 | 3/2009 | Bertolero et al. | |
| 2009/0076537 A1 | 3/2009 | Bertolero | |
| 2009/0281541 A1 | 11/2009 | Ibrahim et al. | |

OTHER PUBLICATIONS

Jansen, Erik, et al., "Less Invasive off-pump CABG using a suction device for immobilization: The Octopus method," European Journal of Cardiothoracic surgery 12 (1997) pp. 406-412.

* cited by examiner

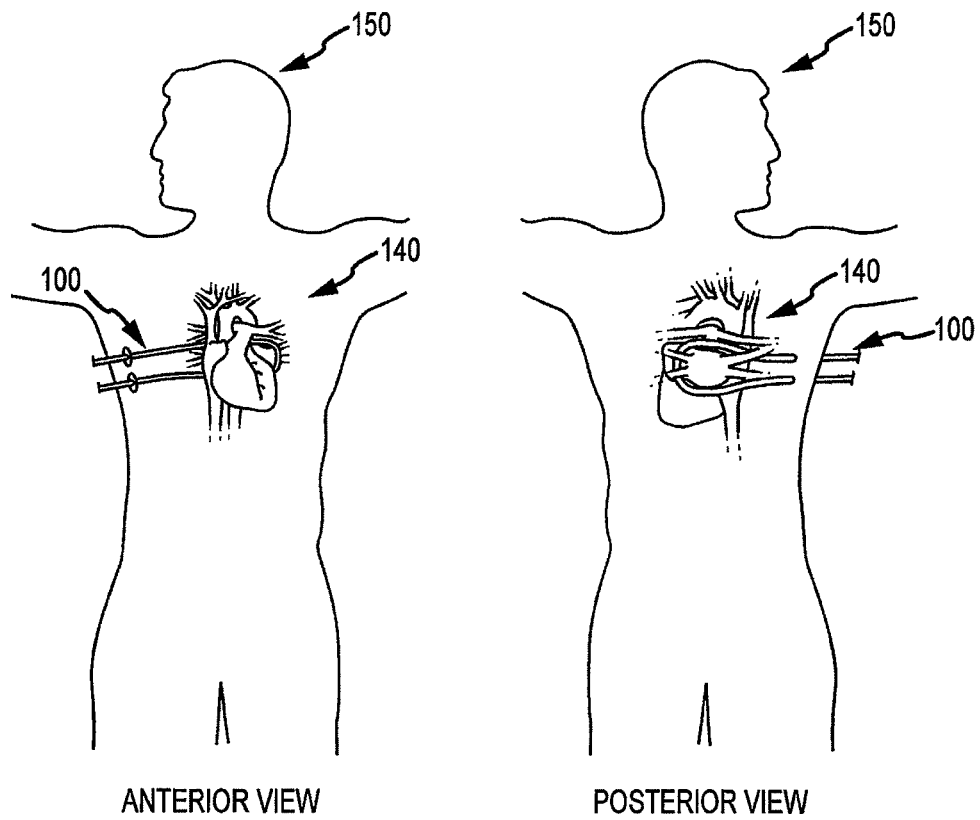
ANTERIOR VIEW
FIG.1
POSTERIOR VIEW
FIG.1A
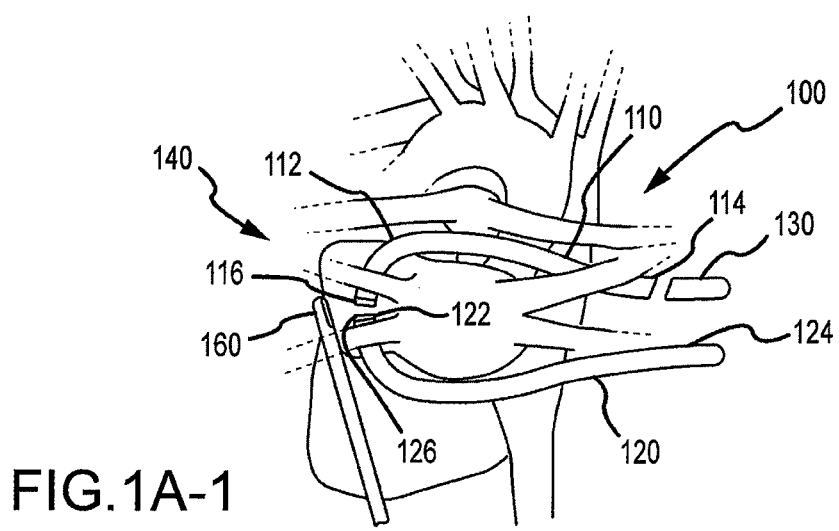
FIG.1A-1

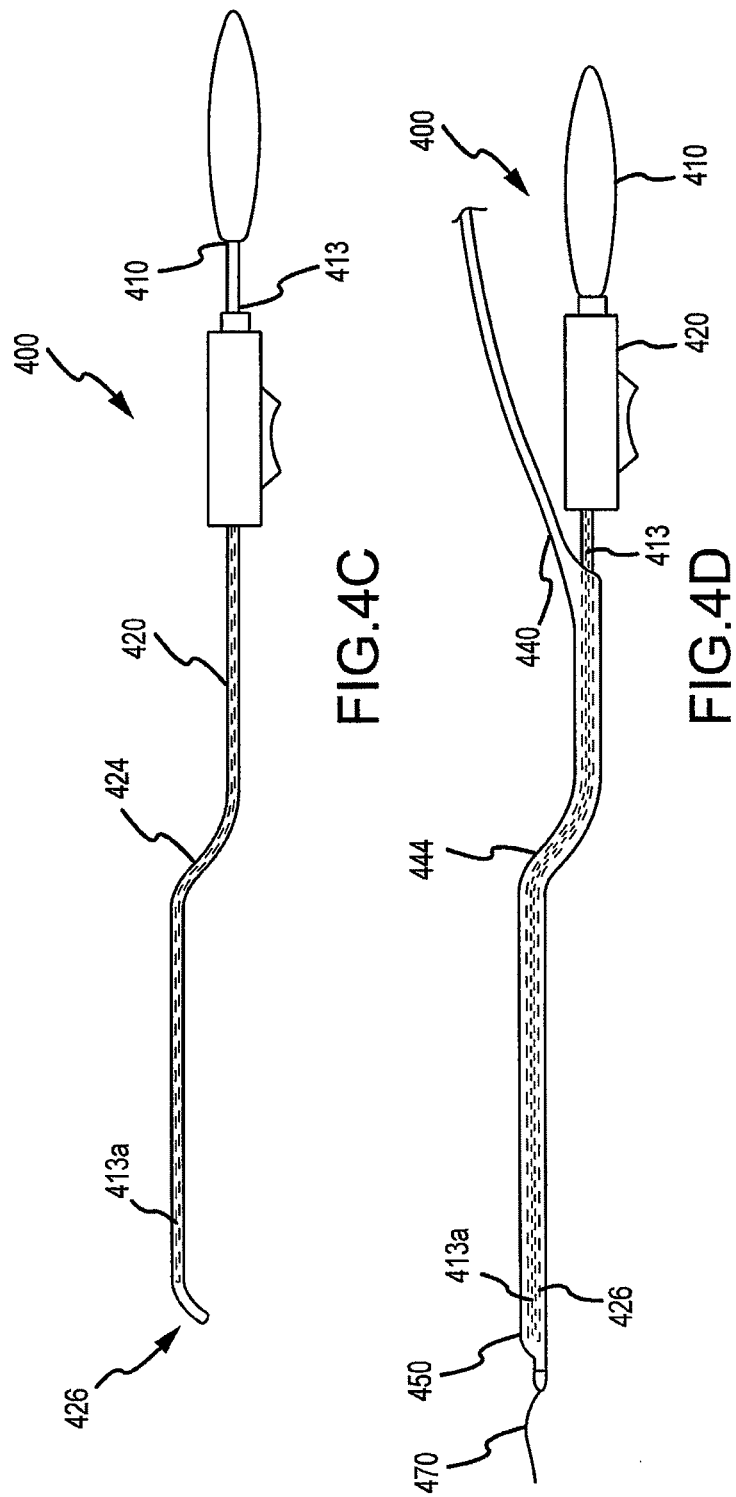

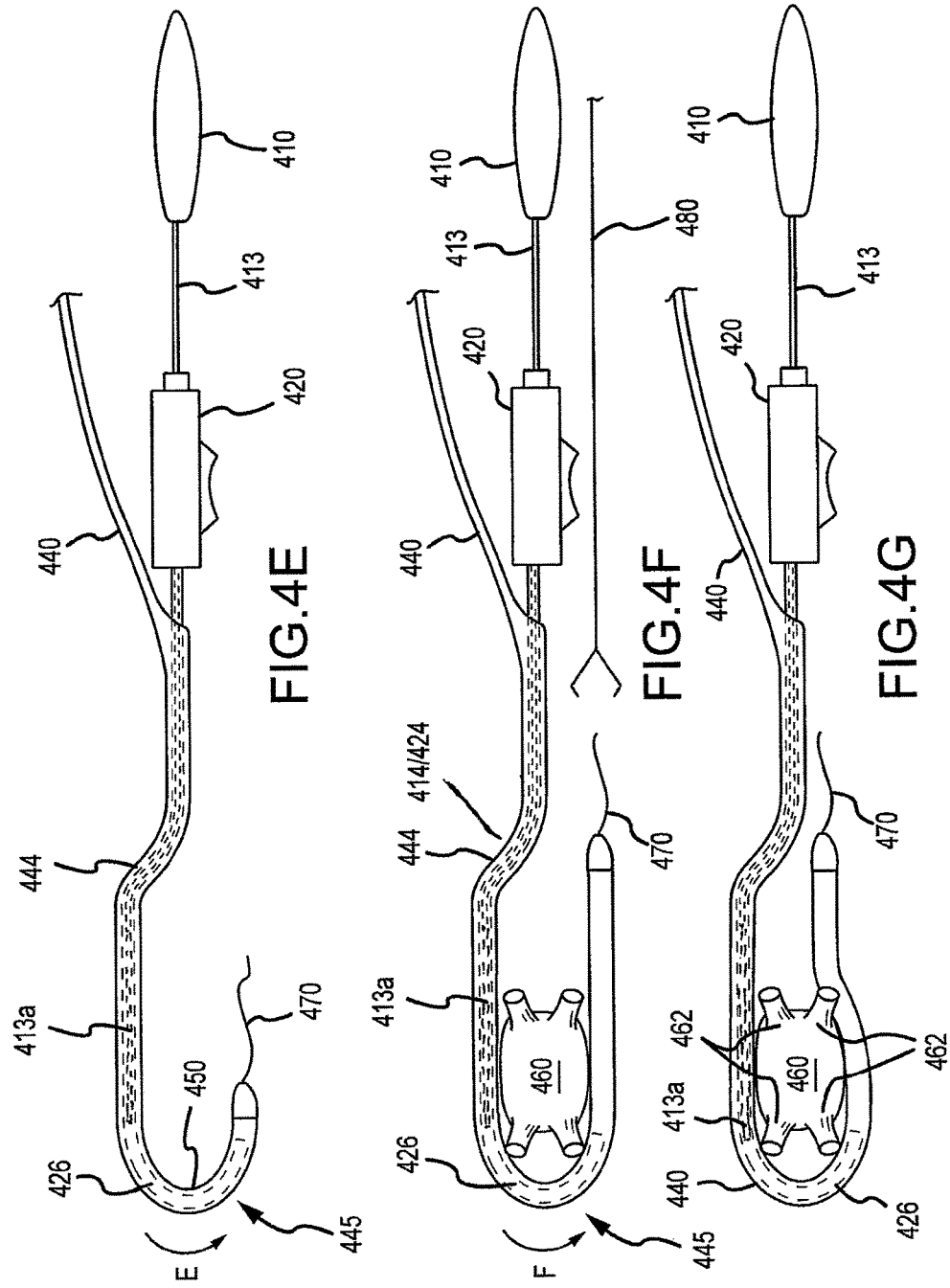

MAGNETIC INTRODUCER SYSTEMS AND METHODS

CROSS-REFERENCES TO RELATED APPLICATIONS

This application is a nonprovisional of, and claims the benefit of the filing date of, U.S. Provisional Patent Application No. 61/015,472, entitled "MAGNETIC INTRODUCER SYSTEMS AND METHODS," filed Dec. 20, 2007, the entire disclosure of which is incorporated herein by reference for all purposes.

This application is related to U.S. Patent Application No. 60/939,201 filed May 21, 2007, the entire disclosure of which is incorporated herein by reference for all purposes.

BACKGROUND OF THE INVENTION

Embodiments of the present invention relate generally to medical devices and methods. More specifically, embodiments relate to devices and methods for positioning a treatment device in a patient.

Medical treatment and surgical methods typically involve a surgeon or operator placing a treatment device at a desired location within a patient. For example, a surgeon can position a cardiac ablation device in the vicinity of a patient's heart, and apply an ablative energy to the epicardial tissue to treat atrial fibrillation and other arrhythmias. Often, treatment devices are difficult to accurately position at an effective location within the patient. Relatedly, surgeons may find it difficult to adequately secure a treatment device at a desired location in the patient. Another shortcoming of currently available surgical techniques is the difficulty of gaining optimal visualization of a surgical or treatment site on the heart or of structures in and around the surgical site. In other words, gaining sufficient visualization to allow the surgeon to accurately manipulate, ablate, or otherwise operate at a specific location within the patient's body is sometimes challenging using current methods and devices. Oftentimes, visualization devices and surgical instruments collide or simply overcrowd a surgical site, reducing a surgeon's room to work in and visualize the surgical site.

Therefore, a need exists for devices, systems, and methods for positioning a treatment device at a desired location in the patient. In some embodiments, devices and methods would provide enhanced techniques for viewing within the body of the patient to facilitate placement of the treatment devices, without crowding the surgical site. Optionally, embodiments may involve improved techniques for attaching or securing a treatment device at a location within a patient. Further, it would be desirable for such methods and devices to be minimally invasive. At least some of these objectives will be met by embodiments of the present invention.

BRIEF SUMMARY OF THE INVENTION

Embodiments of the present invention provide techniques for placing a treatment device at a location within a patient. Such techniques involve the use of introducer devices having coupling mechanisms, and optionally integrated visualization mechanisms, whereby an operator can efficiently and effective manipulate the introducer devices within the patient's body so as to position a treatment device at a desired location. Advantageously, such techniques can be performed in a minimally invasive procedure without crowding the surgical site.

System embodiments are well suited for use in administering ablation treatments to patients. An exemplary system can include an ablation assembly having a flexible ablation member configured to deliver an ablation energy to a tissue of the patient. In some cases, the system includes a placement assembly that can help position and engage the ablation assembly about the patient tissue in a circumferential or semi-circumferential path. In some cases, ablative energy can be administered through the ablation member so as to create a transmural lesion in the cardiac tissue. For example, ablative energy can be applied to form a closed path lesion in the epicardial tissue of the patient.

In a first aspect, embodiments of the present invention provide methods for placing a treatment device at a location within a patient. A method may include, for example, advancing a first introducer into the patient, where the first introducer includes a distal portion and a proximal portion, and the distal portion of the first introducer includes a coupling member. The method may also include advancing a second introducer into the patient, where the second introducer includes a distal portion and a proximal portion, and the distal portion of the second introducer includes a coupling member. Further, the method may include coupling the coupling member of the first introducer and the coupling member of the second introducer, and moving the first introducer and the second introducer while the coupling member of the first introducer and the coupling member of the second introducer are coupled, so as to place a treatment device that is coupled with the proximal portion of the first introducer at a location within the patient. In some methods, the coupling member of the first introducer includes a magnet, the coupling member of the second introducer includes a magnet, and the step of coupling the coupling members includes coupling the distal portion of the first introducer and the distal portion of the second introducer via an attractive magnetic force between the first introducer magnet and the second introducer magnet. Optionally, the second introducer may include a grasping mechanism, and the step of coupling the coupling members may include grasping a distal element of the first introducer with the grasping mechanism of the second introducer. According to some embodiments, methods may include visualizing the distal portion of the first introducer and the distal portion of the second introducer with a visualization device. A treatment device can include an ablation device, and methods may involve creating a transmural lesion in a cardiac tissue of the patient with the ablation device. Some methods include placing an obturator within the patient, and advancing the first introducer along the obturator.

In another aspect, embodiments of the present invention provide systems for providing a treatment to a patient. A system can include a first introducer having a distal portion and a proximal portion, where the distal portion includes a coupling member. The system may also include a second introducer having a distal portion and a proximal portion, where the distal portion includes a coupling member. The system may also include a treatment device configured to be releasably coupled with the proximal portion of the first introducer. In some cases, the coupling member of the first introducer includes a magnet, and the coupling member of the second introducer includes a magnet. In some cases, the coupling member of the second introducer includes a grasping mechanism, and the coupling member of the first introducer includes a distal element that can be grasped by the grasping mechanism. Optionally, the treatment device may include an ablation device. According to some embodiments, a system includes an obturator having a shape, where the obturator is configured to bend the first introducer toward the shape of the obturator. An obturator may include a stiffening rod and a handle.

In still another aspect, embodiments of the present invention encompass methods for placing a treatment device at a location within a patient that include advancing an introducer and a visualization device into the patient. The introducer can include a distal portion and a proximal portion, and the distal portion of the introducer can include a coupling member. The visualization device can include a distal portion and a proximal portion, and the distal portion of the visualization device can include a coupling member and a visualization member. Methods may also include visualizing the distal portion of the introducer with the visualization member of the visualization device, coupling the distal portion of the introducer and the distal portion of the visualization device, and moving the introducer and the visualization device while the distal portion of the introducer and the distal portion of the visualization device are coupled, so as to place a treatment device that is coupled with the proximal portion of the introducer at a location within the patient. In some cases, the coupling member of the introducer includes a magnet, the coupling member of the visualization device includes a magnet, and the step of coupling the coupling members includes coupling the distal portion of the introducer and the distal portion of the visualization device via an attractive magnetic force between the introducer magnet and the visualization device magnet. Optionally, the visualization device may include a grasping mechanism, and the step of coupling the coupling members can include grasping a distal element of the introducer with the grasping mechanism of the visualization device. In some embodiments, the treatment device includes an ablation device, and methods may include creating a transmural lesion in a cardiac tissue of the patient with the ablation device. According to some embodiments, methods may include placing an obturator within the patient, and advancing the introducer along the obturator.

In yet another aspect, embodiments of the present invention encompass systems for providing a treatment to a patient that include an introducer, a visualization device, and a treatment device. An introducer may include a distal portion and a proximal portion, and the distal portion may include a coupling member. A visualization device may include a distal portion and a proximal portion, and the distal portion may include a coupling member and a visualization member. The treatment device may be configured to be releasably coupled with the proximal portion of the introducer. In some cases, the coupling member of the introducer includes a magnet, and the coupling member of the visualization device includes a magnet. In some cases, the coupling member of the visualization device introducer includes a grasping mechanism, and the coupling member of the introducer includes a distal element that can be grasped by the grasping mechanism. Optionally, a treatment device may include an ablation device. According to some embodiments, a system may include an obturator having a shape, and the obturator can be configured to bend the introducer toward the shape of the obturator. In some cases, an obturator may include a stiffening rod and a handle.

For a fuller understanding of the nature and advantages of the present invention, reference should be had to the ensuing detailed description taken in conjunction with the accompanying drawings.

BRIEF DESCRIPTION OF THE DRAWINGS

FIGS. 4A to 4G show aspects of an obturator treatment or ablation system according to embodiments of the present invention.

DETAILED DESCRIPTION OF THE INVENTION

Embodiments of the present invention provide systems and methods for placing a treatment device within a patient. Exemplary techniques involve advancing a magnetic first introducer into the patient, advancing a magnetic second introducer into the patient, coupling the first introducer with the second introducer via magnetic force, and using the introducer devices to place a treatment device at a desired location within the patient. Optionally, such techniques may involve visualization of the introducers or treatment devices during the procedure. For example, a system for administering an ablation treatment to a patient may include an ablation assembly having a flexible ablation member configured to deliver ablative energy to a tissue of the patient. The system may also include a stabilizer member that helps to hold the ablation member against or near the patient tissue. In some cases, the system includes a positioning or cinching assembly or member that can be used to maneuver the ablation assembly into a desired configuration within the patient's body. For example, the positioning assembly may be used to help position the ablation assembly about the patient tissue in a circumferential path. Often, the ablation assembly includes an ablation electrode for transmitting ablative energy to the patient tissue. Such systems are well suited for delivering ablative energy to the cardiac tissue of a patient, for example to create a transmural lesion in the epicardial tissue. In some cases, transmural lesions are in the form of a closed path.

Figure 1B:
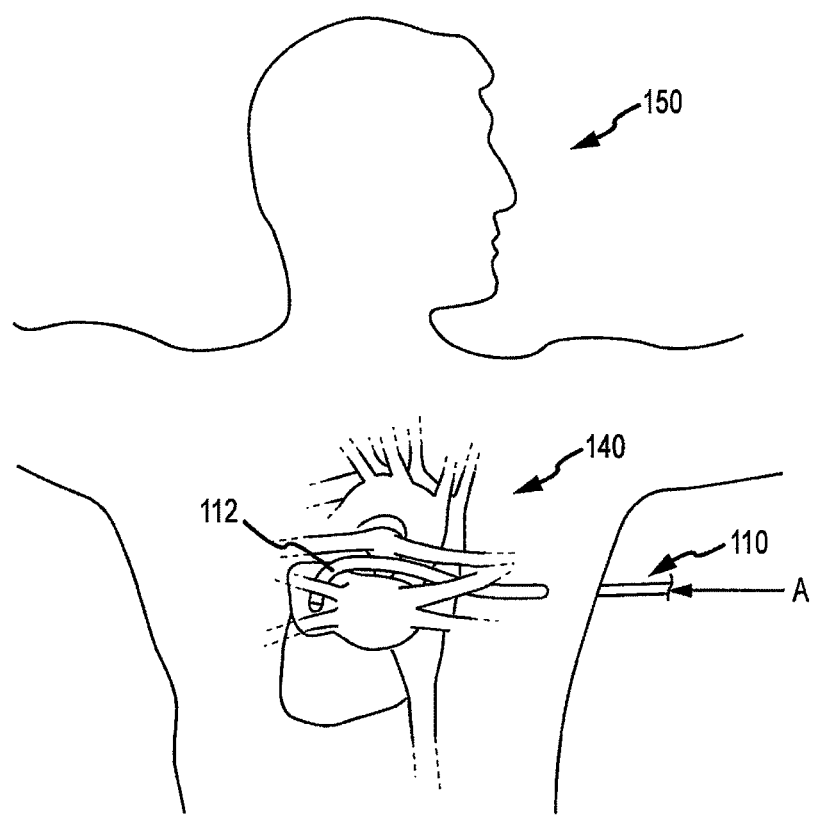
FIGS. 1 to 1E show aspects of an introducer system according to embodiments of the present invention.
Figure 1C:
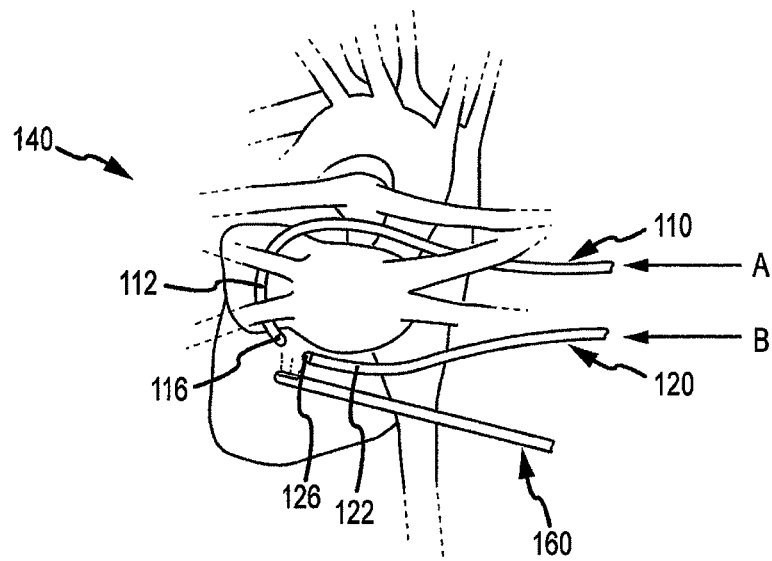
Figure 1D:
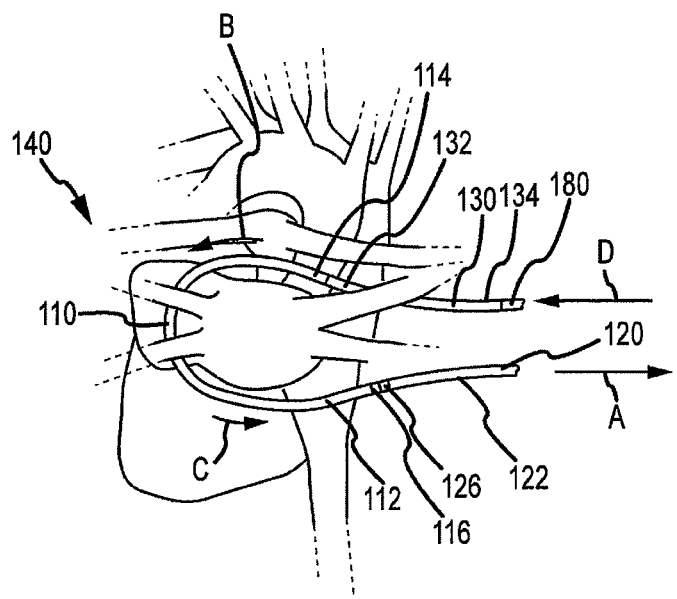
Figure 1E:
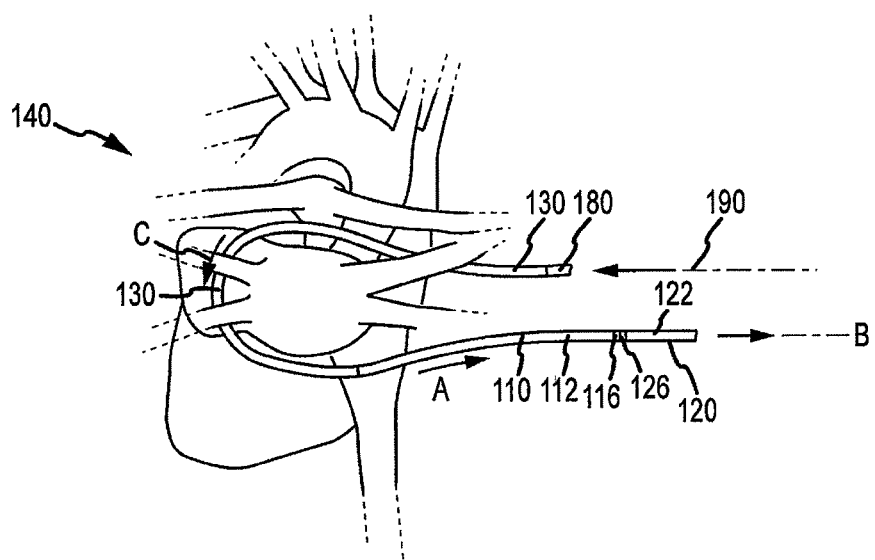

Turning now to the drawings, FIGS. 1 to 1E show an introducer system and method of use according to embodiments of the present invention. FIG. 1 depicts a front or anterior view of a patient and an introducer system 100 placed at a location 140 within the body of a patient 150. FIG. 1A depicts a rear or posterior view of patient 150 and introducer system 100 placed at location 140 within the body of patient 150. The introducer system 100 is also shown in a disassembled state in FIG. 1A-1. Introducer system 100 includes a first introducer device 110, a second introducer device 120, and a visualization device 160. In use, an operator can employ the introducer device and visualization device to position a treatment device 130 at a location 140 in a patient. First introducer device 110 has a distal section 112, a proximal portion 114, and a magnet 116. Typically, magnet 116 is disposed toward distal section 112 of the first introducer device. Similarly, second introducer device 120 has a distal section 122, a proximal portion 124, and a magnet 126. Typically, magnet 126 is disposed toward distal section 122 of the second introducer device. FIG. 1B provides a posterior anatomical view, and illustrates the positioning of first introducer device 110 within patient 150. As shown here, an operator can advance distal section 112 of the first introducer device toward location 140 which has been selected for treatment, as indicated by arrow A. FIG. 1C provides a posterior anatomical view, and depicts a closer view of the treatment location. An operator can continue to advance distal section 112 of the first introducer device toward a desired location as indicated by arrow A. Similarly, the operator can advance distal section 122 of the second introducer device toward location 140 as indicated by arrow B. An operator can also view the first and second introducer devices with visualization device 160. For example, the operator can view distal sections 112 and 122 as the introducer devices are manipulated within the patient's body. Such visualization can assist the operator in bringing distal sections 112 and 122 into proximity with each other, such that first introducer magnet 116 and second introducer magnet 126 can attach or couple. It is understood that first introducer device 110, second introducer device 120, or visualization device 160, or any combination thereof, may be introduced into the patient via one or more incisions placed in any suitable location. Incisions may include subzyphoid incisions, subcostal incisions, intercostal incisions or any other suitable incision or combination of incisions.

As illustrated in the posterior anatomical view provided in FIG. 1D, proximal section 114 of first introducer device 110 can be coupled with a distal section 132 of treatment device 130. When distal sections 112 and 122 are held together via the magnetic force between magnets 116 and 126, the operator can advance treatment device 130 toward location 140. This can be accomplished by moving second introducer device 120 away from treatment location 140 as indicated by arrow A. For example, the operator may grasp the second introducer device and pull it in a direction away from the patient. Optionally, treatment device 130 can be advanced toward location 140 by moving proximal portion 114 of the first introducer device toward the location as indicated by arrow B. In some cases, this may involve moving distal portion 112 of the first introducer device away from the location as indicated by arrow C. Relatedly, in some cases the operator may grasp the treatment device itself, or perhaps a proximal positioner 180 coupled with treatment device 130, so as to manipulate the positioning of the treatment device. Any of these movements, or any combination thereof, can be used to move treatment device 130 toward location 140 as indicated by arrow D. FIG. 1E provides a posterior anatomical view, and shows the positioning of treatment device 130 at location 140, as first and second introducer devices 110, 120, and treatment device 130 are advanced along a positioning path 190, as indicated by arrows A, B, and C, respectively. In this way, a surgeon can use the first and second introducer devices of introducer system 100 to effectively place treatment device 130 within the patient's body.

Visualization device 160 may encompass any of a variety of imaging mechanisms for viewing or detecting the location and orientation of the introducer or treatment devices as they may be situated within or relative to the patient, or relative to other system components. For example, visualization device 160 may include an endoscope, a Transesophageal Echocardiogram (TEE) device, an X-ray fluoroscopy device, or the like. Devices are often manipulated based on monitoring the device location relative to visualized cardiac structures, such as the left or right pulmonary artery, aorta, or pulmonary veins. Transducer inputs from the device, such as electrogram recordings, can also be used to refine the location of the introducer or therapeutic device relative to the tissues being targeted. Exemplary treatments include atrial fibrillation (AF) therapy, Left Atrial Appendage (LAA) exclusion or removal, pulmonary lobectomy or other thoracic cancer therapy, or procedures to safely enter the pericardial space.

Figure 2A:
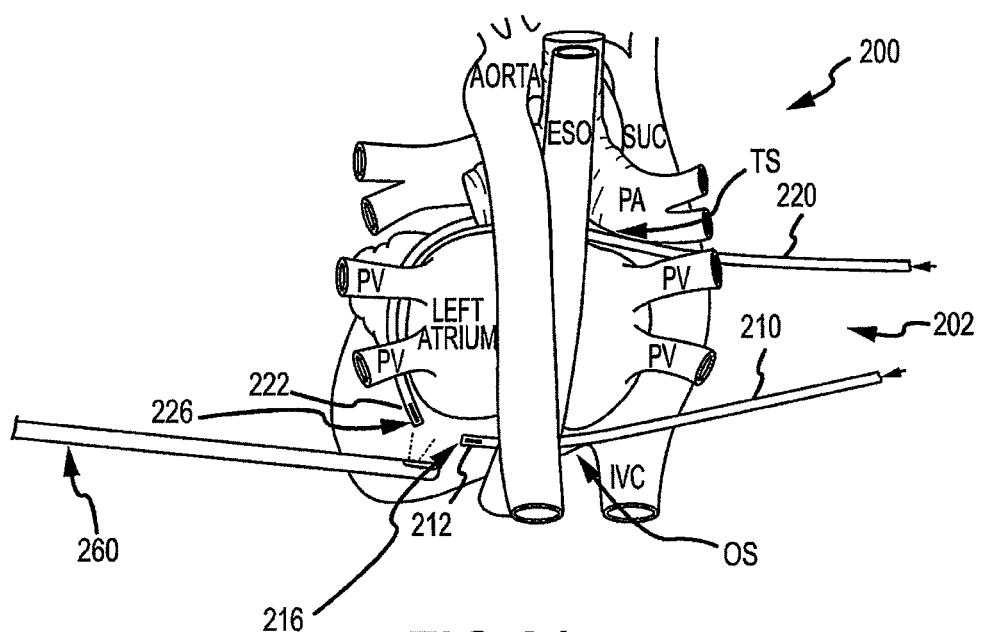
FIGS. 2A to 2C show aspects of an introducer system according to embodiments of the present invention.
Figure 2B:
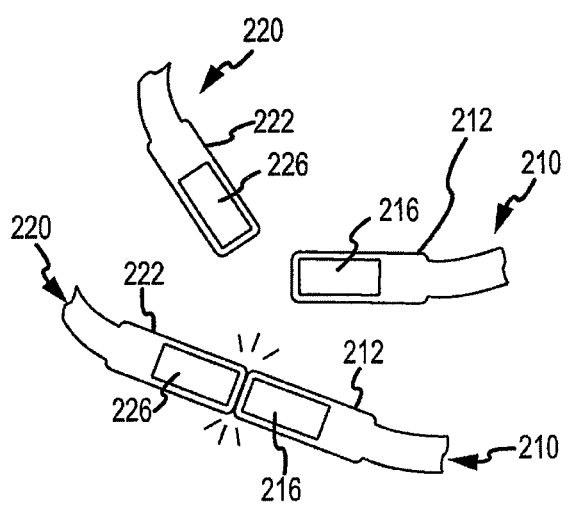
Figure 2C:
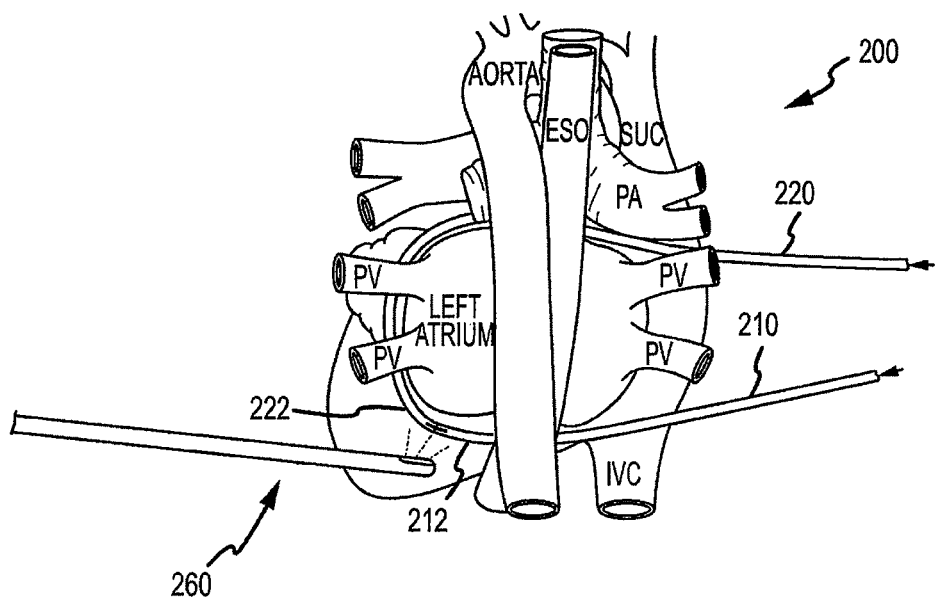

FIGS. 2A to 2C illustrate how an introducer system can be used in a tissue environment of a patient, according to embodiments of the present invention. An ablation or treatment system 200 includes an introducer system 202 having a first introducer device 210 and a second introducer device 220. The treatment system may also include a visualization device 260. First and second introducer devices include a magnetically or mechanically attaching mechanism, whereby a distal end or section 212 of the first introducer device can be attached or coupled with a distal end or section 222 of the second introducer device. For example, the attaching mechanism may include a first magnet 216 disposed toward the distal section of the first introducer device, and a second magnet 226 disposed toward the distal section of the second introducer device. Such configurations can be used in a minimally invasive surgical procedure, so as to position or manipulate an ablation mechanism within the body of a patient. For example, introducer system 202 can be used to move a treatment device about a patient's pulmonary veins (PV). As shown in FIG. 2A, second introducer device 220 can be advanced within a patient, whereby the device enters a first cavity such as a transverse sinus (TS). Similarly, first introducer device 210 can be advanced within a patient, whereby the device enters a second cavity such as an oblique sinus (OS). Optionally, a surgeon or operator may use visualization device 260 to view or detect introducer devices 210, 220 as they are placed within the patient's body. The distal end or section 212 of first introducer device 210, the distal end or section 222 of second introducer device 220, or both, can be manipulated so as to couple one with the other. For example, an attractive force between first magnet 216 and second magnet 226 can effectively couple or attach distal end 212 with distal end 222.

As shown in FIG. 2B, the magnets can have self aligning faces, and the distal ends of first introducer device 210 and second introducer device 220 can have rounded or blunted edges. Typically, magnets have a dipolar magnetic field, and therefore opposite ends of magnets are attracted to each other. Due to the self aligning configuration, the magnetic dipole of first magnet 216 tends to align or orient itself with the opposed polarity of the magnetic dipole of second magnet 226. In use, when an operator determines that the distal ends of first introducer device 210 and second introducer device 220 are coupled, the operator can manipulate the introducer system or the treatment or ablation system to a position as desired. In some cases, an operator can determine that the distal ends are coupled by visual confirmation. Optionally, the operator can view or detect a coupling between distal sections 212, 222 by using visualization device 260. In some cases, an operator can hear or feel the distal ends snap together. FIG. 2C depicts ablation or treatment system 200 disposed within the patient's body, where distal section 212 of first introducer device 210 is coupled with distal section 222. After the distal ends are coupled, an operator can advance a treatment device toward a desired location within the patient, in a manner similar to that described with reference to FIGS. 1D and 1E.

Figure 3A:
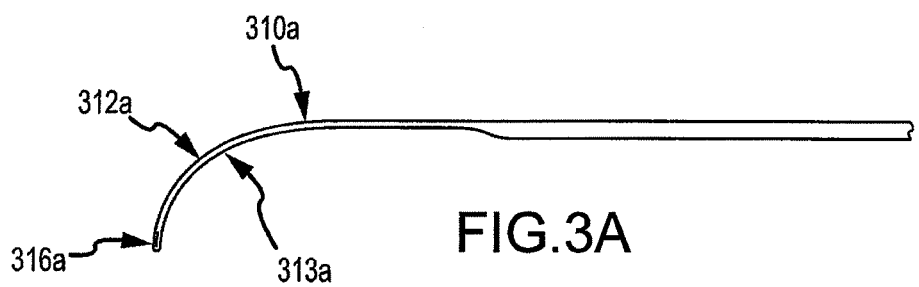
FIGS. 3A to 3D show aspects of treatment or ablation introducer devices according to embodiments of the present invention.
Figure 3B:
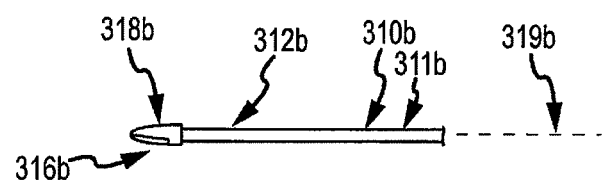
Figure 3C:
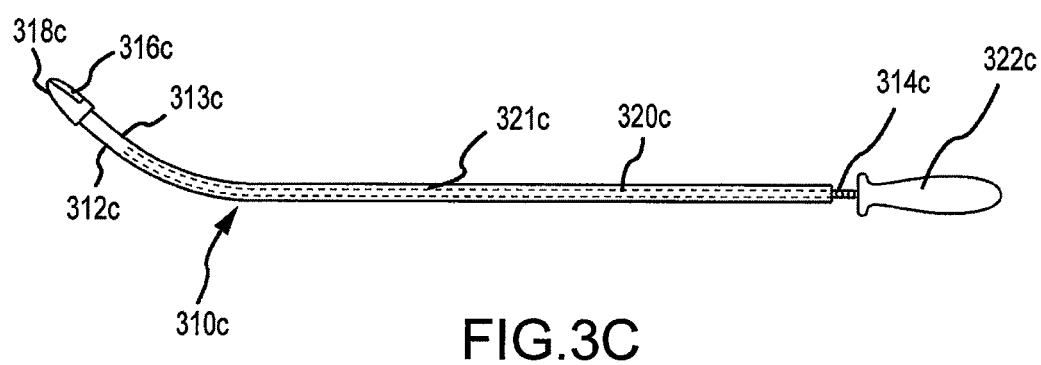
Figure 3D:
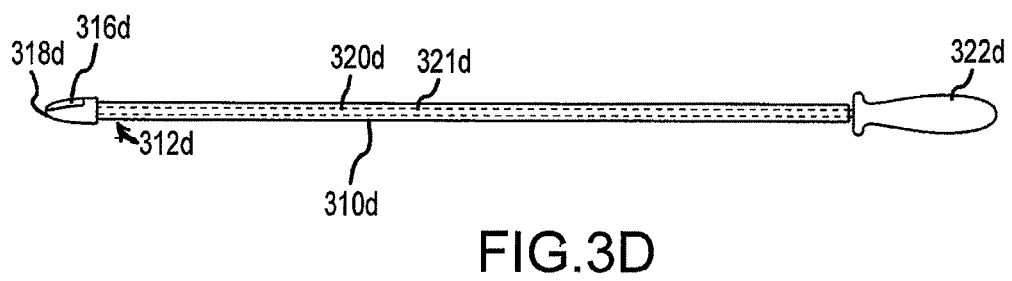

FIGS. 3A to 3D show aspects of visualization systems, scopes, or introducer devices according to embodiments of the present invention. FIG. 3A shows that a magnet or other attachment mechanism 316a can be disposed at or toward a distal end or portion 312a of a device introducer 310a. In some embodiments, distal end or portion 312a can include a preformed bend 313a. FIG. 3B shows that a magnet or other attachment mechanism 316b can be disposed at or toward a distal end or portion 312b of a device introducer 310b, where the device introducer includes a visualization element 318b. The position of magnet or attachment mechanism 316b may be offset. For example, magnet or attachment mechanism 316b may laterally offset from a central longitudinal axis 319b defined by a shaft 311b of the introducer device. According to FIG. 3C, an obturator 320c can be inserted into or moved along device introducer 310a. Obturator 320c may include a handle 322c disposed at or toward a proximal end or portion 314c and a stiffening rod 321c. Device introducer 310a can include a visualization mechanism 318a and an attachment mechanism 316c such as a magnet disposed at or toward a distal end or portion 312c of introducer device 310c. The obturator 320c shown here is partially inserted into device introducer 310c, such that stiffening rod 321c, which is less flexible than distal portion 312c of introducer device 310c, operates to straighten only a portion of a preformed bend 313c. According to embodiments of the present invention, introducer device 310c may be malleable or flexible. Obturator 320c can optionally include a connector configured to interface with another portion of the system or other devices, at or near the proximal end of obturator 320c. As noted below with regard to FIGS. 4A-4G, a straight, preformed, bent, or malleable obturator may be inserted inside a flexible introducer from or near the proximal end of the introducer.

Introducer device 320c may have a preformed bend 313c at or near the distal end to allow a desired curve to form as a stiffer obturator is withdrawn or inserted during a particular phase of a procedure. The obturator may be fully or partially inserted or withdrawn completely as needed or desired. According to FIG. 3D, obturator 320d may be further or fully inserted into introducer device 310d, such that the preformed bend of introducer device 310d is substantially straightened. As depicted here, obturator 320d includes a handle 322d and a stiffening rod 321d. Introducer device 310d includes a distal section or portion 312d having a visualization mechanism 318d and an attachment mechanism 316d such as a magnet. Obturator 320d may be flexible, stiff, preformed, or malleable. In some cases, an obturator includes one or more stiff wires. As noted elsewhere herein, the position of a magnet or attachment mechanism may be offset. In some cases, offsetting the position of the magnet or attachment mechanism can provide an operator with an optimized field of view, depending on the geometric configuration of a visualization system. In some embodiments, the terms "introducer device", "scope", and "visualization system" maybe used interchangeably. Such devices may be flexible, or fixed.

Figure 4A:
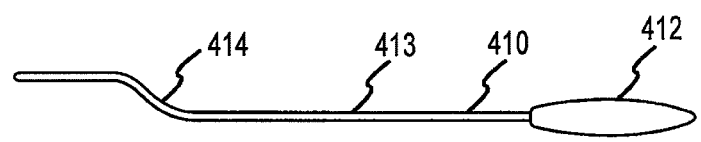
Figure 4B:
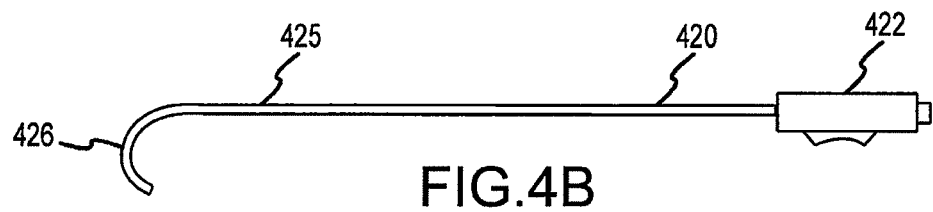

FIGS. 4A to 4G show aspects of an obturator treatment or ablation system according to embodiments of the present invention. Such positioning systems can involve an obturator and a probe that when used in conjunction with an ablation system can create a substantially mid-length curved portion that is positionally controlled independently from the axial, longitudinally slidable position of an ablation system and a distal curved sheath or probe portion that is controlled manually and not affected by the position of the obturator. FIG. 4A illustrates an obturator 410 having a handle 412 coupled with a stiffening rod 413. As shown here, preformed stiffening rod 413 includes a preformed bend 414. A preformed bend 414 may be created out of material sufficiently stiff to perform its function, which can include bending a deformable introducer device and optionally a treatment device, yet be springy or elastic enough without excessively yielding when subjected to influences of the introducer device or treatment device. Such a configuration allows system insertion through and placement within a patient anatomy, utilizing a material that is sufficiently stiff to perform its function yet malleable enough to be formed into an advantageous or desired curve or shape. Exemplary materials include a malleable metal, such as stainless steel. FIG. 4B illustrates a steerable sheath or introducer device 420 having a handle 422 and a flexible casing 425. The flexible casing may include in its distal, steerable portion a preformed curve or bend 426. As noted below, bend 426 may be initially straightened to facilitate insertion into the body by an integral steering mechanism that includes a pull wire, for example, or by the insertion of the obturator 410. According to some embodiments, therefore, an introducer device having an integral steering mechanism may be referred to as a steerable introducer, a deflectable introducer, or the like. Distal curve 426 is independent of a curve 424 produced by a mid-length bend 414 in the obturator stiffening rod, as depicted in FIG. 4C. In use, an operator can construct the obturator assembly 400 by inserting obturator stiffening rod 413 into sheath or introducer device 420. In this sense, obturator assembly 400 can be construed to include obturator 410 and introducer device 420. Typically, the obturator stiffening rod is more rigid than the sheath or introducer device casing 424. Accordingly, the shape of casing 425 can conform with the shape of the bent stiffening rod, so as to provide a complementary bend 424 in the casing. In some cases, both an obturator and a steerable sheath or introducer device can be provided in a pre-assembled configuration. In either case, whether manually constructed or pre-assembled, the obturator stiffening rod 413 can be axially slidable within or along the sheath or introducer device 420 so that the curve 414 of the obturator 410 can be positioned as desired within the sheath or introducer device 420. As shown in FIG. 4C, obturator 410 can be inserted into introducer device 420 to a sufficient depth such that bend 426 of introducer device is partially straightened. In this way, the distal portion 413a of stiffening rod 413 straightens or otherwise deforms part of the introducer device distal curve 426.

As depicted in FIG. 4D, an ablation or treatment system 440 can slide over the combined sheath or introducer device and obturator assembly 400, so as to create a bend 444 in the ablation or treatment system. The ability to independently slide the obturator 410 axially within the sheath or introducer device 420 provides placement of the relatively stationary curve 444 desired for the ablation system 440 as the ablation system is advanced over the stationary obturator assembly 400. Alternatively, the curve in the obturator assembly 400 which corresponds to obturator curve 414 and introducer device curve 424 may be advanced within a relatively stationary ablation system 440 so as to provide an advantageous or desired placement during the procedure. The combined obturator assembly 400 and ablation system 440 can be inserted across the left atrium of a patient's heart, for example. Obturator 410 can remain inserted into introducer device 420 to a sufficient depth such that bend 426 of introducer device remains substantially straightened. [In this way, distal portion 413a of stiffening rod 413 straightens or otherwise deforms the introducer device distal curve 426.

As depicted in FIG. 4E, an operator can retract obturator 410 from probe 420 to a sufficient depth, such that probe bend 426 recovers or returns toward its original configuration. Consequently, probe bend 426 forces the corresponding section of ablation system 440 to adopt a similar bent or curved shape 445. With obturator 410 only partially advanced within the sheath 420, an operator can negotiate the turn at the far side of the heart by flexing the steerable distal portion of the probe at bend 426 along with the distal portion 450 of the ablation assembly 440, as indicated by arrow E. According to the illustration in FIG. 4F, the operator can engage or grasp distal element 470 of ablation system 440 with engaging element 480, and advance ablation system 440 distally along the stationary obturator assembly 400, as indicated by arrow F. In this manner it is possible to maintain curve 444 in ablation assembly 440 as produced by the combined bend 414 of obturator 410 and bend 424 of probe 420, and also maintain curve 445 in ablation assembly 440 as produced by bend 426 of probe 420, while minimizing pressure and friction on adjacent tissues 460 such as the heart. In some embodiments, distal or grasping element 470 includes a string or tape which the operator can grasp with a maneuvering mechanism 480 such as a pair of forceps. Optionally, grasping element 470 may include a magnetic element which the operator can engage with a maneuvering mechanism 480 such as a matching magnetic device. As shown in FIG. 4G, placement of ablation system 440 against the pulmonary veins is facilitated by advancing obturator 410 within sheath or introducer device 420 such that bend 444 is disposed at or near the tissue to make or enhance tissue contact. As shown in this figure, the contour of the distal bends are similar to or conform to the shape of the tissue 460.

Figure 5A:
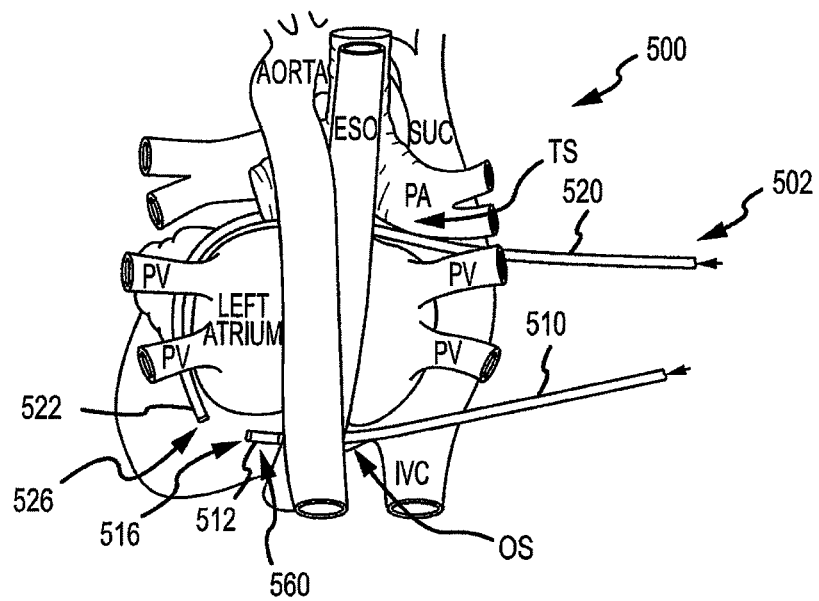
FIGS. 5A to 5C illustrate aspects of an introducer system according to embodiments of the present invention.
Figure 5B:
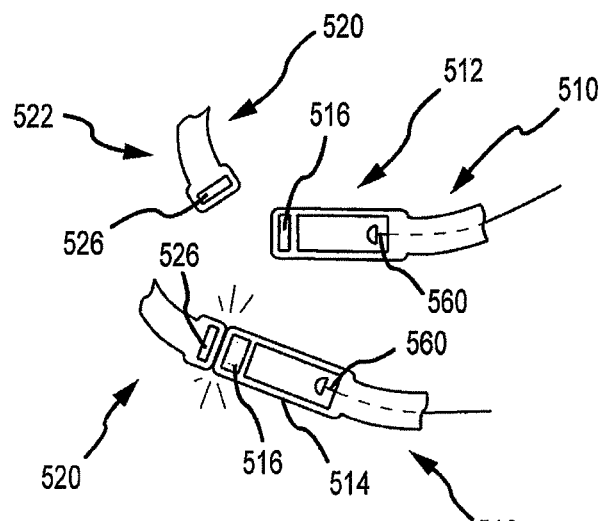
Figure 5C:
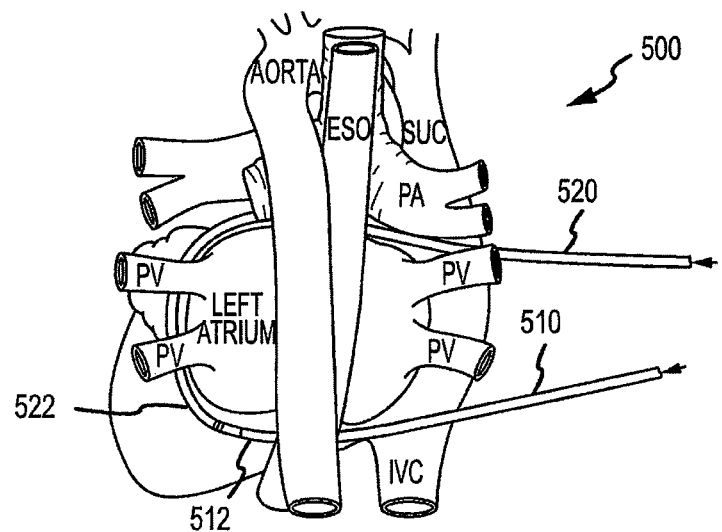

FIGS. 5A to 5C illustrate how an introducer system can be used in a tissue environment of a patient, according to embodiments of the present invention. An ablation or treatment system 500 includes an introducer system 502 having a first introducer device 510 and a second introducer device 520. The treatment system may also include a visualization device 560 incorporated into or integrated with either the first introducer device or the second introducer device. First and second introducer devices include a magnetically or mechanically attaching mechanism, whereby a distal end or section 512 of the first introducer device can be attached or coupled with a distal end or section 522 of the second introducer device. For example, the attaching mechanism may include a first magnet 516 disposed toward the distal section of the first introducer device, and a second magnet 526 disposed toward the distal section of the second introducer device. Such configurations can be used in a minimally invasive surgical procedure, so as to position or manipulate an ablation mechanism within the body of a patient. For example, introducer system 502 can be used to move or position a treatment device about a patient's pulmonary veins (PV). As shown in FIG. 5A, second introducer device 520 can be advanced within a patient, whereby the device enters a first cavity such as a transverse sinus (TS). Similarly, first introducer device 510 can be advanced within a patient, whereby the device enters a second cavity such as an oblique sinus (OS). Optionally, a surgeon or operator may use visualization device 560 to view or detect introducer devices 510, 520 as they are placed within the patient's body. The distal end or section 512 of first introducer device 510, the distal end or section 522 of second introducer device 520, or both, can be manipulated so as to couple one with the other. For example, an attractive force between first magnet 516 and second magnet 526 can effectively couple or attach distal end 512 with distal end 522.

As shown in FIG. 5B, the magnets can have self aligning faces, and the distal ends of first introducer device 510 and second introducer device 520 can have rounded or blunted edges. Typically, a magnet has a dipolar magnetic field, and therefore opposite ends of magnets are attracted to each other. Due to the self aligning configuration, the magnetic dipole of first magnet 516 tends to align or orient itself with the opposed polarity of the magnetic dipole of second magnet 526. In use, when an operator determines that the distal ends of first introducer device 510 and second introducer device 520 are coupled, the operator can manipulate the introducer system or the treatment or ablation system to a position as desired. In some cases, an operator can determine that the distal ends are coupled by visual confirmation. Optionally, the operator can view or detect a coupling between distal sections 512, 522 by using visualization device 560. For example, distal section 512 may include a transparent material 514 that allows the operator to see the surrounding tissue environment with the visualization device. According to the embodiment depicted here, an operator can use visualization device 560 to determine the location or orientation of second introducer device 520, for example relative to the location or orientation of first introducer device 510. In this way, use of the visualization device 560 can assist the operator in maneuvering first magnet 516 and second magnet 526 into close proximity, so as to provide the desired magnetic coupling. In some cases, an operator can hear or feel the distal ends snap together. FIG. 5C depicts ablation or treatment system 500 disposed within the patient's body, where distal section 512 of first introducer device 510 is coupled with distal section 522 of second introducer device 520. After the distal ends are coupled, an operator can advance a treatment device toward a desired location within the patient, in a manner similar to that described with reference to FIGS. 1D and 1E.

Figure 6:
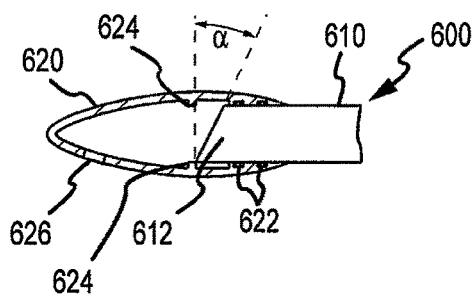
FIG. 6 shows aspects of a visualization system according to embodiments of the present invention.

FIG. 6 shows a cross-section of a visualization system 600 which can be used for providing or enhancing device placement visualization. For example, such visualization can be carried out in conjunction with a tissue ablation treatment. Visualization system 600 can include a scope 610 and a cap 620. Scope 610 includes a distal end 612, which in some cases is beveled at an angle α. In some embodiments, angle α can be within a range from about 30 degrees to about 45 degrees. Scope 610 can be a straight scope, a rigid scope, or both, for example. In some embodiments, scope 610 includes an endoscope. Cap 620 can include a tip having a bullet shape, a cone shape, a dome shape, and the like. In some embodiments, cap 620 may present an asymmetric shape. Optionally, a cap may be shaped for optimized visualization of a tissue. Often, cap 620 includes a clear or transparent portion or material through which a lens of scope 610 can visualize the surrounding environment. In this way, cap 620 can operate to expand the visualization capacity, or the field of view, of scope 610. In use, cap 620 can be advanced into or against tissue, and can separate tissue. Accordingly, tissue which presses on cap 620, or is otherwise near cap 620, can be visualized. Cap 620 can allow a user or operator to visualize an increased amount of tissue, or an increased surface area of tissue, as compared to a similar scope which does not include cap 620. In some cases, an operator can use visualization system 600 for orientation purposes, for treatment purposes, for therapeutic purposes, and the like. Cap 620 allows an operator to gain an enhanced awareness of an operating space within a patient's body. For example, an operator may use visualization system 600 to determine how close a particular instrument or device is to a pulmonary vein. Such techniques can be helpful when applying a treatment to a site that is near, but not on, a pulmonary vein. An operator will also find such approaches useful when connecting or coupling introducer devices together, for example via the magnetic attraction techniques as described herein.

Cap 620 may include a stop 624. In use, stop 624 typically contacts distal end 612 of scope 610 when cap 620 is disposed on scope 610. The location or position of stop 624 on cap 620 can be selected so as to control or adjust the distance between a distal end, or some other visualization portion, of cap 620, and a lens of scope 610. Different scopes may have different focal lengths, and selection of a desired stop 624 configuration can allow cap 620 to provide a particular viewing effect on a patient's tissue. For example, by placing stop 624 at a certain distance from a distal end or viewing portion of cap 620, it may be possible to allow an operator to view tissue which contacts the distal end or viewing portion of cap 620 with a maximum clarity or distinctness, so that the tissue is in focus.

Cap 620 can protect a lens of scope 610 from unwanted contact with fluid. Toward this end, cap 620 may include one or more sealing mechanism 622. For example, sealing mechanism 622 may include an o-ring. Cap 620 may be releasably attached with scope 610. For example, it may be possible to snap together, and to snap apart, cap 620 and scope 610. In some cases, cap 620 includes an attachment mechanism 626, which can be used to attach or couple visualization system 600 with another device or implement. This attachment or coupling can be a releasable attachment. In use, cap 620 of visualization system 600 allows an operator to visualize an operating space within a patient. When an operator views a device or implement to which the operator wishes to couple with visualization system 600, the operator can utilize attachment mechanism 626 so as to couple visualization system 600 with the desired device or implement. For example, attachment mechanism 626 can include a magnet, and the device or implement can include a material which is attracted to the magnet. The operator can advance or place the magnet near the device or implement, so as to create a releasable coupling between the magnet and the device or implement.

Figure 7:
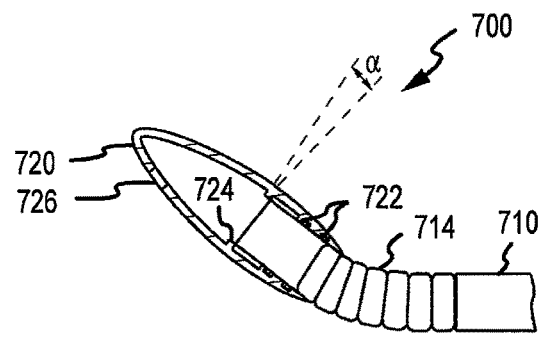
FIG. 7 shows aspects of a visualization system according to embodiments of the present invention.

FIG. 7 shows a cross-section of a visualization system 700 which can be used for providing or enhancing device placement visualization. For example, such visualization can be performed in conjunction with a tissue ablation treatment. Visualization system 700 can include a scope 710 and a cap 720. Scope 710 includes a distal end 712, which in some cases is not beveled at an angle $\alpha$. In some embodiments, angle $\alpha$ can be about 0 degrees. Scope 710 can also include a flexible zone or portion 714. Scope 710 can be a curved scope, a flexible scope, or both, for example. In some embodiments, scope 710 includes an endoscope. Cap 720 can include a tip having a bullet shape, a cone shape, a dome shape, and the like. In some embodiments, cap 720 may present an asymmetric shape. Optionally, a cap may be shaped for optimized visualization of a tissue. Often, cap 720 includes a clear or transparent portion or material through which a lens of scope 710 can visualize the surrounding environment. In this way, cap 720 can operate to expand the visualization capacity, or the field of view, of scope 710. In use, cap 720 can be advanced into or against tissue, and can separate tissue. Accordingly, tissue which presses on cap 720, or is otherwise near cap 720, can be visualized. Cap 720 can allow a user or operator to visualize an increased amount of tissue, or an increased surface area of tissue, as compared to a similar scope which does not include cap 720. In some cases, an operator can use visualization system 700 for orientation purposes, for treatment purposes, for therapeutic purposes, and the like. Cap 720 allows an operator to gain an enhanced awareness of an operating space within a patient's body. For example, an operator may use visualization system 700 to determine how close a particular instrument or device is to a pulmonary vein. Such techniques can be helpful when applying a treatment to a site that is near, but not on, a pulmonary vein. An operator will also find such approaches useful when connecting or coupling introducer devices together, for example via the magnetic attraction techniques as described herein.

Cap 720 may include a stop 724. In use, stop 724 typically contacts distal end 712 of scope 710 when cap 720 is disposed on scope 710. The location or position of stop 724 on cap 720 can be selected so as to control or adjust the distance between a distal end, or some other visualization portion, of cap 720, and a lens of scope 710. Different scopes may have different focal lengths, and selection of a desired stop 724 configuration can allow cap 720 to provide a particular viewing effect on a patient's tissue. For example, by placing stop 724 at a certain distance from a distal end or viewing portion of cap 720, it may be possible to allow an operator to view tissue which contacts the distal end or viewing portion of cap 720 with a maximum clarity or distinctness, so that the tissue is in focus.

Cap 720 can protect a lens of scope 710 from unwanted contact with fluid. Toward this end, cap 720 may include one or more sealing mechanism 722. For example, sealing mechanism 722 may include an o-ring. Cap 720 may be releasably attached with scope 710. For example, it may be possible to snap together, and to snap apart, cap 720 and scope 710. In some cases, cap 720 includes an attachment mechanism 726, which can be used to attach or couple visualization system 700 with another device or implement. This attachment or coupling can be a releasable attachment. In use, cap 720 of visualization system 700 allows an operator to visualize an operating space within a patient. When an operator views a device or implement to which the operator wishes to couple with visualization system 700, the operator can utilize attachment mechanism 726 so as to couple visualization system 700 with the desired device or implement. For example, attachment mechanism 726 can include a magnet, and the device or implement can include a material which is attracted to the magnet. The operator can advance or place the magnet near the device or implement, so as to create a releasable coupling between the magnet and the device or implement.

Figure 8:
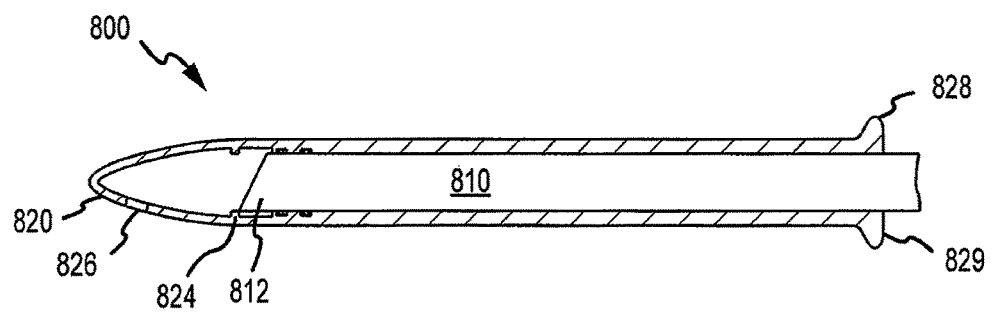
FIG. 8 shows aspects of a visualization system according to embodiments of the present invention.

FIG. 8 shows a cross-section of a visualization system 800 which can be used for providing or enhancing device placement visualization. For example, such visualization can be performed in conjunction with a tissue ablation treatment. Visualization system 800 can include a scope 810 and a cap 820. Scope 810 includes a distal end 812, which in some cases is not beveled at an angle α. In some embodiments, angle α can be about 30 degrees to about 45 degrees. Scope 810 can be a straight scope, a rigid scope, or both, for example. In some embodiments, scope 810 includes an endoscope. Cap 820 can include a tip having a bullet shape, a cone shape, a dome shape, and the like. In some embodiments, cap 820 may present an asymmetric shape. Optionally, a cap may be shaped for optimized visualization of a tissue. Often, cap 820 includes a clear or transparent portion through which a lens of scope 810 can visualize the surrounding environment. In this way, cap 820 can operate to expand the visualization capacity, or the field of view, of scope 810. In use, cap 820 can be advanced into or against tissue, and can separate tissue. Accordingly, tissue which presses on cap 820, or is otherwise near cap 820, can be visualized. Cap 820 can allow a user or operator to visualize an increased amount of tissue, or an increased surface area of tissue, as compared to a similar scope which does not include cap 820. In some cases, an operator can use visualization system 800 for orientation purposes, for treatment purposes, for therapeutic purposes, and the like. Cap 820 allows an operator to gain an enhanced awareness of an operating space within a patient's body. For example, an operator may use visualization system 800 to determine how close a particular instrument or device is to a pulmonary vein. Such techniques can be helpful when applying a treatment to a site that is near, but not on, a pulmonary vein. Cap 820 can be moved relative to scope 810 or relative to body tissue. In some cases, cap 820 can be rotated relative to scope 810 or relative to body tissue. An operator may effect such movement via a handle 828 of cap 820. An operator will also find such approaches useful when connecting or coupling introducer devices together, for example via the magnetic attraction techniques as described herein.

Cap 820 may include a stop 824. In use, stop 824 can contact distal end 812 of scope 810 when cap 820 is disposed on scope 810. The location or position of stop 824 on cap 820 can be selected so as to control or adjust the distance between a distal end, or some other visualization portion, of cap 820, and a lens of scope 810. Different scopes may have different focal lengths, and selection of a desired stop 824 configuration can allow cap 820 to provide a particular viewing effect on a patient's tissue. For example, by placing stop 824 at a certain distance from a distal end or viewing portion of cap 820, it may be possible to allow an operator to view tissue which contacts the distal end or viewing portion of cap 820 with a maximum clarity or distinctness, so that the tissue is in focus.

Cap 820 can protect a lens of scope 810 from unwanted contact with fluid. Toward this end, as shown here the length of cap 820 can be such that fluid is not present at a proximal end 829 of cap 820. Cap 820 may be releasably attached with scope 810. For example, it may be possible to snap together, and to snap apart, cap 820 and scope 810. In some cases, cap 820 includes an attachment mechanism or instrument mount 826, which can be used to attach or couple visualization system 800 with another device or implement. This attachment or coupling can be a releasable attachment. In use, cap 820 of visualization system 800 allows an operator to visualize an operating space within a patient. When an operator views a device or implement to which the operator wishes to couple with visualization system 800, the operator can utilize attachment mechanism 826 so as to couple visualization system 800 with the desired device or implement. For example, attachment mechanism 826 can include a magnet, and the device or implement can include a material which is attracted to the magnet. The operator can advance or place the magnet near the device or implement, so as to create a releasable coupling between the magnet and the device or implement. In some embodiments, all or part of cap 820 can be constructed of a flexible material, such as an elastomer. In some embodiments, cap 820 is rigid. Similarly, scope 810 may be flexible or rigid. In some embodiments, a distal end of cap 820 is rigid, and a proximal end of cap 820 is flexible.

Figure 9A:
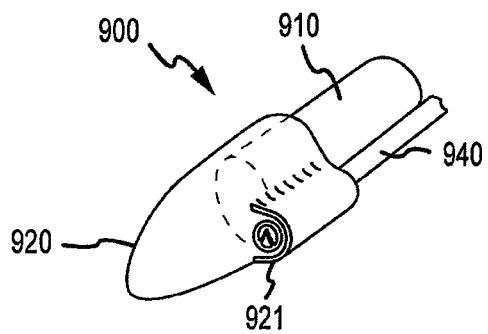
FIGS. 9A to 9C show aspects of a visualization system according to embodiments of the present invention.
Figure 9B:
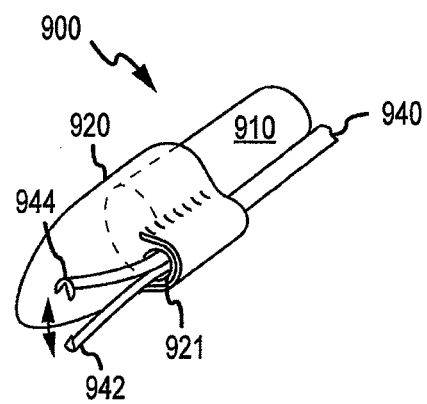
Figure 9C:
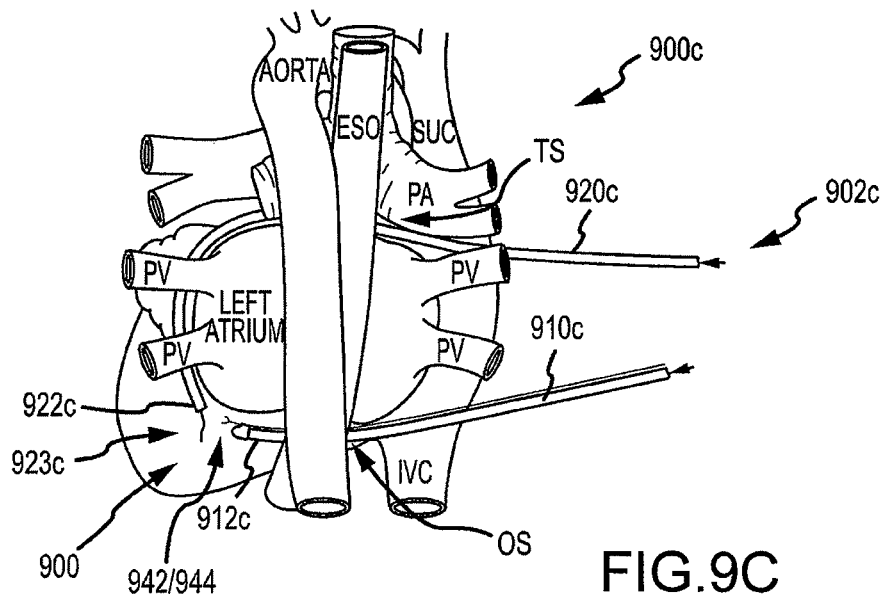

FIGS. 9A to 9C show aspects of a visualization system 900 which can be used for providing or enhancing device placement visualization. For example, such visualization can be performed in conjunction with a tissue ablation treatment. Visualization system 900 can include a scope 910 and a cap 920. Scope 910 and cap 920 can include any feature or component of the scopes and caps discussed herein, for example the scopes and caps depicted in FIGS. 6 to 8. As shown here, cap 920 can include an attachment mechanism channel 921 adapted to receive an attachment mechanism such as a grasping device 940. Grasping device 940 can include a pair of spring loaded jaws 942, 944. When pushed against a spring force as depicted in FIG. 9B, grasping device 940 can protrude out of channel 921, and jaws 942, 944 can open or separate. When retracted as depicted in FIG. 9A, jaws 942, 944 close together, and grasping device 940 withdraws into channel 921. In use, an operator can advance grasping device 940 out of cap 920 and place open jaws 942, 944 on a desired item to be grasped. The operator can then withdrawn grasping device 940 into cap 920, thereby clamping jaws 942, 944 on the item.

In some embodiments, an operator can push grasping device 940 against a spring force so that grasping device 940 protrudes out of cap channel 921, thereby opening the jaws. The jaws can be used to grasp a hook, or a fabric, or a component on a device or introducer for a device which the operator wishes to grasp. Often, the operator may grasp a distal end of such a device or introducer. Accordingly, visualization system 900 can be used in a minimally invasive surgical procedure by an operator to find a device, attach to the device, and then to manipulate or retract the device. FIG. 9C shows how an introducer system 900c can be used in conjunction with a visualization system 900 according to embodiments of the present invention. Ablation or treatment system 900c includes an introducer system 902c having a first introducer device 910c and a second introducer device 920c. The treatment system also includes visualization system 900 incorporated into or integrated with a distal section 912c of the first introducer device. Visualization system 900 can be attached or coupled with a string, tape, or other attachment mechanism 923, which may be attached with distal section 922c of second introducer device 920c. Such configurations can be used in a minimally invasive surgical procedure, so as to position or manipulate an ablation mechanism within the body of a patient. For example, introducer system 902c can be used to move or position a treatment device about a patient's pulmonary veins (PV). As shown here, second introducer device 920c can be advanced within a patient, whereby the device enters a first cavity such as a transverse sinus (TS). Similarly, first introducer device 910c can be advanced within a patient, whereby the device enters a second cavity such as an oblique sinus (OS). Optionally, a surgeon or operator may use visualization system 900 to view or detect introducer devices 910c, 920c as they are placed within the patient's body. The distal end or section 912c of first introducer device 910c, the distal end or section 922c of second introducer device 920c, or both, can be manipulated so as to couple one with the other. In use, when an operator determines that the distal ends of first introducer device 910*c* and second introducer device 920*c* are coupled, the operator can manipulate the introducer system or the treatment or ablation system to a position as desired. In some cases, an operator can determine that the distal ends are coupled by visual confirmation. Optionally, the operator can view or detect a coupling between distal sections 912*c*, 922*c* by using visualization system 900. For example, distal section 912*c* may include a transparent material that allows the operator to see the surrounding tissue environment with the visualization system. According to the embodiment depicted here, an operator can use visualization system 900 to determine the location or orientation of second introducer device 920*c*, for example relative to the location or orientation of first introducer device 910*c*. In this way, use of the visualization system 900 can assist the operator in maneuvering the grasping jaws 942, 944 and the tape or string 923*c* into close proximity, whereby the desired coupling may be effected. After the distal ends are coupled, an operator can advance a treatment device toward a desired location within the patient, in a manner similar to that described with reference to FIGS. 1D and 1E.

Figure 10A:
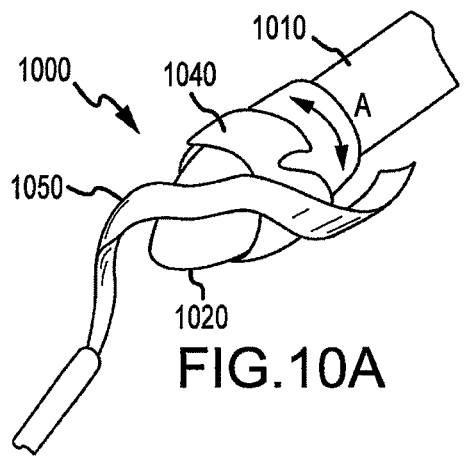
FIGS. 10A and 10B show aspects of a visualization system according to embodiments of the present invention.
Figure 10B:
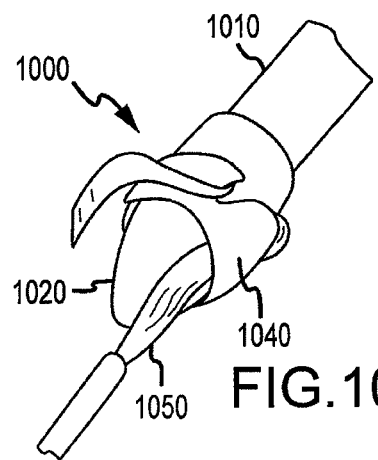

FIGS. 10A and 10B show aspects of a visualization system 1000 which can be used for providing or enhancing device placement visualization. For example, such visualization can be performed in conjunction with a tissue ablation treatment. Visualization system 1000 can include a scope 1010 and a cap 1020. Scope 1010 and cap 1020 can include any feature or component of the scopes and caps discussed herein, for example the scopes and caps depicted in FIGS. 6 to 8. As shown here, the visualization system can include a grasping device 1040, such as a fin or wedge. In use, an operator can place grasping device 1040 near a distal grasping element or introducer tape 1050, and rotate the grasping device as indicated by arrow A. In this way, the grasping device can securely attach with the distal grasping element. As shown in FIG. 10A, when tape 1050 comes into view grasping device 1050 can be rolled to snag tape on a hook or fin of the device, which can then be rolled back to produce a roll of tape. As shown in FIG. 10B, grasping device 1050 can include a wedging shape that holds the tape under tension. Accordingly, visualization system 1000 can be used in a minimally invasive surgical procedure by an operator to find a device, attach to the device, and then to manipulate or retract the device.

Figure 11:
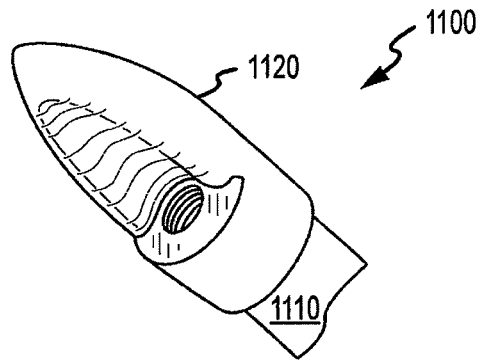
FIG. 11 shows aspects of a visualization system according to embodiments of the present invention.

FIG. 11 shows aspects of a visualization system 1100 which can be used for providing or enhancing device placement visualization. For example, such visualization can be performed in conjunction with a tissue ablation treatment. Visualization system 1100 can include a scope 1110 and a cap 1120. Scope 1110 and cap 1120 can include any feature or component of the scopes and caps discussed herein, for example the scopes and caps depicted in FIGS. 6 to 8. As shown in FIG. 11, a concave shape of cap 1120 can facilitate use of a working channel of scope 1110.

Figure 12A:
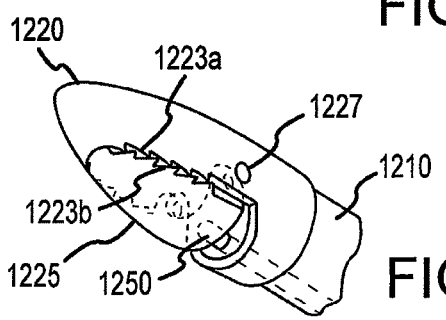
FIGS. 12A to 12C show aspects of a visualization system according to embodiments of the present invention.
Figure 12B:
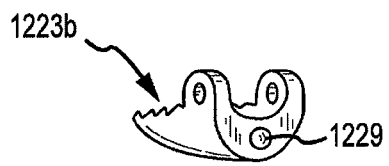
Figure 12C:
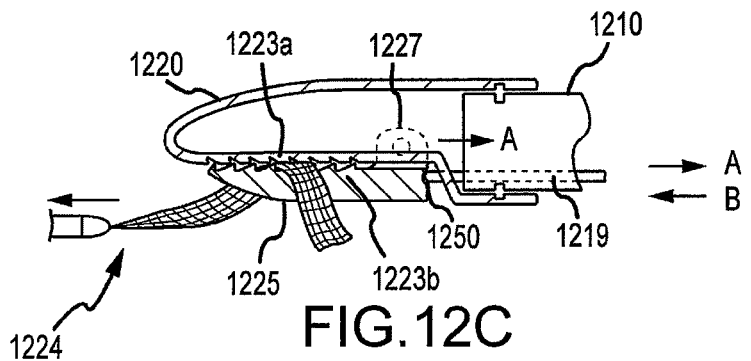

FIGS. 12A to 12C illustrate aspects of a visualization system 1200 which can be used for providing or enhancing device placement visualization. For example, such visualization can be performed in conjunction with a tissue ablation treatment. Visualization system 1200 can include a scope 1210 and a cap 1220. Scope 1210 and cap 1220 can include any feature or component of the scopes and caps discussed herein, for example the scopes and caps depicted in FIGS. 6 to 8. As shown in FIG. 12A, the body of cap 1220 includes a grasping portion 1223*a*, and a jaw 1225 of cap 1220 includes a corresponding or complementary grasping portion 1223*b*. The body of cap 1220 is coupled with jaw 1225 via a hinge or pivot 1227, as depicted in FIG. 12C. According to FIGS. 12A to 12C, a pocket, attachment point, or divot 1229 of jaw 1225 can be aligned with a working channel 1219 of scope 1210, and a push pull mechanism or axial member 1250 can be disposed in working channels 1219. When axial member 1250 is advanced distally through working channel 1219, for example, the distal section of axial member 1250 can contact and transmit force to jaw divot 1229, thereby closing the bringing the grasping portions 1223*a*, 1223*b* toward each other. In some embodiments, this configuration may be well suited for use with an angled scope, as compared to a forward looking scope, due to the desired field of view provided by cap 1220. In use, push pull mechanism 1250 can be pulled or retracted as indicated by arrow A so as to open jaw 1225. An operator can manipulate jaw 1225 and the body of cap 1220 about a tape or distal end of a device or introducer. Push pull mechanism 1250 can then be pushed or advanced as indicated by arrow B so as to close jaw 1225, thereby grasping the tape, device, introducer, or other implement 1224.

Figure 13A:
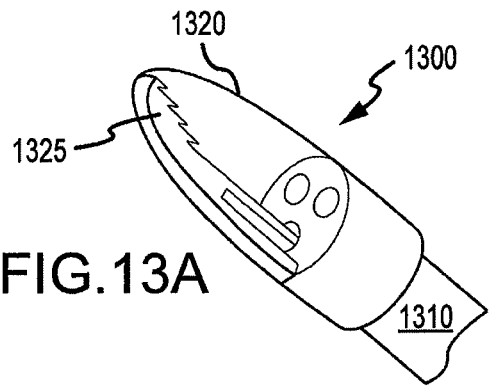
FIGS. 13A to 13D show aspects of a visualization system according to embodiments of the present invention.
Figure 13B:
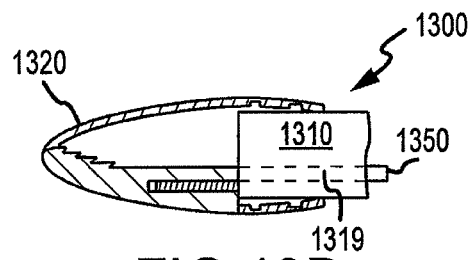
Figure 13C:
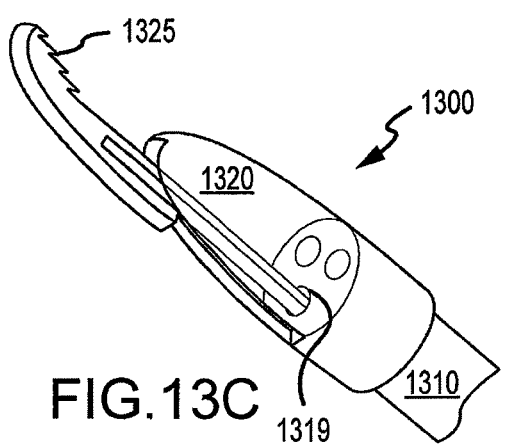
Figure 13D:
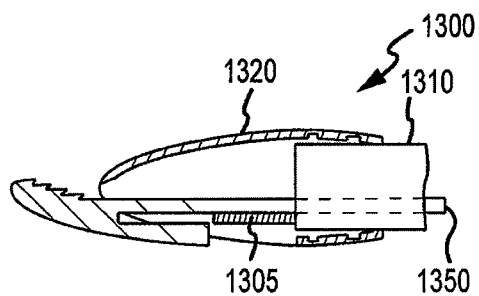

FIGS. 13A to 13D illustrate aspects of a visualization system 1300 which can be used for providing or enhancing device placement visualization. For example, such visualization can be performed in conjunction with a tissue ablation treatment. Visualization system 1300 can include a scope 1310 and a cap 1320. Scope 1310 and cap 1320 can include any feature or component of the scopes and caps discussed herein, for example the scopes and caps depicted in FIGS. 6 to 8. According to FIG. 13A, cap 1320 includes a retractable underslung jaw 1325, shown here in a closed or retracted position. FIG. 13B provides a cross section side view of visualization system 1300. Jaw 1325 can have a push pull mechanism 1350 attached thereto, and disposed within a working channel 1319 of scope 1310. In use, push pull mechanism 1350 can be advanced so as to open jaw 1325, as shown in FIGS. 13C and 13D. An operator can manipulate jaw 1325 so as to snag a tape or distal end of a device or introducer. Push pull mechanism 1350 can then be retracted so as to close jaw 1325, thereby firmly grasping the tape, device, introducer, or other implement. In some embodiments, visualization system 1300 includes an anti-roll guidance rib 1305. In some embodiments, the body of cap 1320 includes a toothed configuration which is complementary to the toothed configuration of jaw 1325.

Figure 14A:
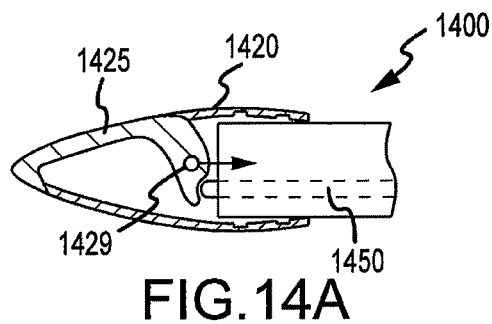
FIGS. 14A and 14B show aspects of a visualization system according to embodiments of the present invention.
Figure 14B:
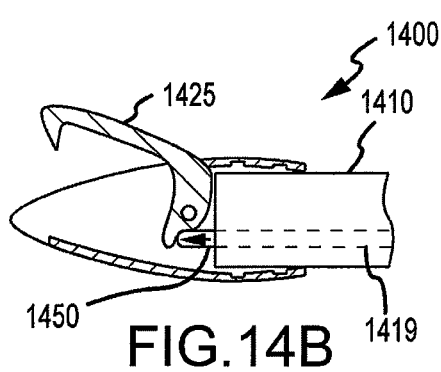

FIGS. 14A and 14B illustrate aspects of a visualization system 1400 which can be used for providing or enhancing device placement visualization. For example, such visualization can be performed in conjunction with a tissue ablation treatment. Visualization system 1400 can include a scope 1410 and a cap 1420. Scope 1410 and cap 1420 can include any feature or component of the scopes and caps discussed herein, for example the scopes and caps depicted in FIGS. 6 to 8. According to FIG. 14A, cap 1420 includes a pivoting overhung toothed jaw 1425, shown here in a closed or retracted position. Jaw 1425 can have an activating mechanism 1450 or a similar axial member attached thereto, and disposed within a working channel 1419 of scope 1410. In use, cap 1420 includes a pivot 1429 that is configured to provide a neutral jaw position under tension, such that there is no tendency for jaw 1425 to open. Activating mechanism 1450 can be advanced distally, as shown in FIG. 14B, so as to swing jaw 1425 about pivot 1429, toward an open configuration. In this configuration, jaw 1425 is disposed outside of the external cone or dome shaped contour of the cap body. An operator can manipulate jaw 1425 so as to snag a tape or distal end of a device or introducer. Activating mechanism 1450 can then be retracted so as to allow jaw 1425 to close, thereby firmly grasping the tape, device, introducer, or other implement. In some embodiments, the body of cap 1420 includes a toothed configuration which is complementary to the toothed configuration of jaw 1425.

Many of the visualization system embodiments disclosed herein include a scope having a working channel, and an activating mechanism or push pull rod which can sit at least partially within the working channel. An operator can cause the activating mechanism to retract or advance, so as to open and close a distal grasping mechanism of the visualization system. In exemplary embodiments, the visualization system includes a cap having a bullet, dome, cone, or similar profile. For example, a cap may present a flat top bullet profile, or a truncated cone profile. In some cases, a cap may present a bulged profile or a mushroom profile. Typically, cap includes a rounded or blunted distal section, so as to avoid cutting tissue when placed within a patient's body. In some cases, a cap is integrated with the scope. In some cases, the cap can be releasably attached with the scope. Often, a scope includes a working channel, and the visualization system includes an activating mechanism that can be disposed at least partially within the working channel. Activating mechanisms can be operated to manipulate grasping members or mechanisms of the visualization system. Often, a cap, a grasping mechanism, an activating mechanism, or any combination thereof, can be configured such that the activating mechanism can be aligned within the working channel when the cap is coupled with the scope. In addition to grasping or attaching mechanisms, any of a variety of other tools may be disposed on or coupled with the cap body, and activated or controlled via an activating mechanism housed at least partially within a working channel of the scope.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A system for creating a lesion in an epicardial tissue of a patient with ablative energy, comprising:
   a first introducer having a distal portion comprising a pre-formed bend and a proximal portion each extending along a longitudinal axis of the first introducer where the distal portion further comprises a first flat distal surface, and where the distal portion comprises a first coupling member;
   a second introducer having a distal portion and a proximal portion each extending along a longitudinal axis of the second introducer, where the distal portion further comprises a second flat distal surface, and where the distal portion comprises a second coupling member; and
   a treatment device having an ablation assembly that includes an ablation member configured to deliver an ablation energy that creates the lesion in the epicardial tissue of the patient,
   wherein the treatment device is configured to be releasably coupled with the proximal portion of the first introducer,
   wherein the first coupling member of the first introducer comprises a magnet adjacent to the first flat distal surface, and the second coupling member of the second introducer comprises a magnet in the second flat distal surface, wherein the magnet of the first introducer has a magnetic dipole and the magnet of the second introducer has a magnetic dipole, and wherein attraction between the first introducer magnet and the second introducer magnet operates to align the first introducer magnet dipole with the second introducer magnet dipole such that when positioned adjacently the first flat distal surface engages the second flat distal surface,
   wherein the first and second introducers are configured to translate along their respective longitudinal axes while the respective coupling members are joined, and
   wherein coupling between the proximal portion of the first introducer and the treatment device, in combination with coupling between the first and second introducers provided by their respective magnets, is effective to move the treatment device toward a treatment location on the epicardial tissue when the second introducer is moved away from the treatment location on the epicardial tissue.

2. The system as in claim 1, further comprising an obturator having a shape, wherein the obturator is configured to bend the first introducer toward the shape of the obturator.

3. The system as in claim 2, wherein the obturator comprises a stiffening rod and a handle.

4. The system as in claim 1, wherein the ablation member is a flexible ablation member configured to deliver the ablation energy to the epicardial tissue of the patient.

5. The system as in claim 1, wherein the ablation member comprises an ablation electrode for transmitting the ablation energy to the epicardial tissue of the patient.

6. The system as in claim 5, wherein the ablation energy is sufficient to create a transmural lesion in the epicardial tissue of the patient.

7. The system as in claim 1, wherein the treatment device comprises a distal section, and the proximal section of the first introducer device is coupled with the distal section of the treatment device.

8. The system as in claim 1, wherein the ablation member comprises a flexible ablation electrode.

9. The system as in claim 1, wherein the proximal portion of the first introducer comprises a first coupling mechanism, the treatment device comprises a second coupling mechanism, the second coupling attachment mechanism of the treatment device is configured to be releasably coupled with the first coupling mechanism of the first introducer, and coupling between the first coupling mechanism of the first introducer and the second coupling mechanism of the treatment device, in combination with coupling between the first and second introducers provided by their respective magnets, is effective to move the treatment device toward a treatment location on the epicardial tissue when the second introducer is moved away from the treatment location on the epicardial tissue.

10. The system as in claim 1, wherein the distal portion of the first introducer comprises a visualization element.

11. The system as in claim 10, wherein the visualization element of first introducer is disposed proximal to the first introducer magnet.

12. The system as in claim 1, wherein the distal portion of the second introducer comprises a visualization element.

13. The system as in claim 12, wherein the visualization element of second introducer is disposed proximal to the second introducer magnet.

14. The system as in claim 1, wherein the first introducer magnetic dipole is perpendicular to the first flat distal surface, and wherein the second introducer magnetic dipole is perpendicular to the second flat distal surface.

* * * * *